United States Patent [19]

Boullet et al.

[11] Patent Number: 4,779,462
[45] Date of Patent: Oct. 25, 1988

[54] APPARATUS FOR THE AUTOMATIC MEASUREMENT OF THE APPARENT DENSITY OF THE MUD IN A LIQUID, SYSTEM FOR THE AUTOMATIC MEASUREMENT OF THE PONSAR INDEX OF SUCH A MUD USING THE APPARATUS AND PROCESS FOR MEASURING SAID INDEX

[75] Inventors: Joseph Boullet, Nanteuil-le-Haudoin; Jean-François Cotro, Vernouillet; Philippe De Jongh, Compiegne; Philippe Hours, Alfortville; Thomas Peaucelle, Neuilly sur Seine, all of France

[73] Assignee: Commissariat a l'Energie Atomique, Paris, France

[21] Appl. No.: 888,367

[22] Filed: Jul. 23, 1986

[30] Foreign Application Priority Data

Jul. 23, 1985 [FR] France ................... 85 11235

[51] Int. Cl.⁴ ............................................. G01N 9/12
[52] U.S. Cl. ....................................... 73/444; 73/614; 73/448
[58] Field of Search ............... 73/447, 448, 453, 61.4, 73/32 R, 450, 444; 364/558

[56] References Cited

U.S. PATENT DOCUMENTS

| 756,702 | 4/1904 | Porter ...................... 73/444 |
| 3,839,909 | 10/1974 | Sanden .................... 364/558 |
| 4,000,657 | 1/1977 | Ponsar ...................... 73/448 |
| 4,131,019 | 12/1978 | Krauss ...................... 73/453 |
| 4,313,340 | 2/1982 | Schniewind ............... 73/61.4 |
| 4,318,296 | 3/1982 | Parker et al. ............. 73/61.4 |
| 4,674,322 | 1/1987 | Stangeland ............... 73/32 R |

FOREIGN PATENT DOCUMENTS 761880 11/1956 United Kingdom .

Primary Examiner—Stewart J. Levy
Assistant Examiner—Hezron E. Williams
Attorney, Agent, or Firm—Oblon, Fisher, Spivak, McClelland & Maier

[57] ABSTRACT

Apparatus for the automotive measurement of the apparent density of mud or sludge contained in a liquid, and a system for the automatic measurement of the PONSAR index and a process for measuring said index. The apparent density of one liter of clarified liquid is obtained with the aid of electronic means for measuring the immersion difference, in a clarified liquid reservoir, of a bottle successively filled with mud and clarified liquid. Detection means make it possible to measure the mud volume decanted or settled in ½ hour in a cylinder filled with one liter of mud-containing liquid and 1.5 liters of clarified liquid. Thus, the calculation of the volume/weight ratio then gives the PANSAR index.

17 Claims, 11 Drawing Sheets

APPARATUS FOR THE AUTOMATIC MEASUREMENT OF THE APPARENT DENSITY OF THE MUD IN A LIQUID, SYSTEM FOR THE AUTOMATIC MEASUREMENT OF THE PONSAR INDEX OF SUCH A MUD USING THE APPARATUS AND PROCESS FOR MEASURING SAID INDEX

BACKGROUND OF THE INVENTION

The present invention relates to an apparatus for automatically measuring the apparent density of a mud or sludge contained in a liquid, a system for the automatic measurement of the Ponsar index of such a mud using the apparatus and a process for measuring said index. It more particularly applies to the operation of waste water purification stations operating on the activated mud or sludge principle (biological purification or clarification).

French Pat. No. 2284108 already discloses a process for measuring the Ponsar index of a mud contained in a liquid, as well as equipment for measuring said index. A definition will be given of the Ponsar index hereinafter. Such equipment is also marketed by the HYDROCURE company.

Said process and said equipment suffer from the disadvanage of being manual, therefore requiring a relatively long and therefore expensive intervention on the part of an operator.

SUMMARY OF THE INVENTION

The object of the present invention is to obviate this disadvantage by proposing an apparatus for the automatic measurement of the apparent density of a mud contained in a liquid, a system for the automatic measurement of the Ponsar index of such a mud using said apparatus, together with a process for measuring said index used in said system.

The invention more specifically relates to an apparatus for measuring the apparent density of a mud contained in a liquid, wherein it comprises a container, means for filling the container with clarified liquid and for emptying the same, a bottle able to float in the container, filled with clarified liquid, when the bottle is empty, means for the displacement of the bottle for bringing the latter into the clarified liquid of the container and to remove the same, means for filling with clarified liquid, liquid containing mud and emptying the bottle, an electrical measuring system able to supply an electric signal, which is a function of the position of the bottle in the container and an electronic processing system for determining the apparent density of one volume of the liquid containing mud, weighed into the clarified liquid, on the basis of electric signals corresponding to the positions, in the clarified liquid-filled container, of the bottle respectively filled with clarified liquid and mud-containing liquid, by appropriately controlling the filling, emptying and displacement means of the bottle.

Preferably, the bottle has an integrated float and an outer shape making it possible to discharge air bubbles during the immersion of the bottle in the clarified liquid.

In an advantageous embodiment of the invention, the bottle has a conical bottom, a cylindrical outer wall and an inner wall defining between them a space which is tightly sealed.

Preferably, the bottle is made from a material which, when it is immersed in the clarified liquid does not absorb the latter or, conversely, is rapidly saturated with said clarified liquid. The term "material which rapidly saturates" is understood to mean a material saturating during a very short time t compared with time $t_1$ during which the bottle remains in the clarified liquid of the container (t being e.g. less than approximately 0.1 $t_1$).

Preferably, the bottle displacement means also comprise a boat able to support the bottle and having holes enabling the clarified liquid to circulate, together with means for displacing the boat.

In a particular embodiment of the apparatus according to the invention, the electric measurement system comprises a coil, which is fixed with respect to the container, a metal rod rendered integral with the bottle and able to form a core for the coil and slide in the latter when the bottle is displaced in the container, thereby modifying the inductance of the coil, and means for measuring a magnitude which is a function of said inductance and able to supply said electric signal. This magnitude can be the actual inductance and preferably the measuring means comprise an inductance meter.

According to an advantageous embodiment, the apparatus according to the invention also comprises an electrode-based probe for informing the electronic processing system of the filling of the bottle.

The present invention also relates to a system for measuring the Ponsar index of a mud contained in a liquid, wherein it comprises the apparent density measurement system also forming an object of the invention, another container, means for filling with clarified liquid, filling with mud-containing liquid and emptying said other container, electric detection means able to supply other electric signals, which are a function of the mud level decanted or settled in the other container previously filled with clarified liquid and mud-containing liquid and wherein the electronic processing system also serves to determine, on the basis of said other signals, the mud volume decanted or settled in the other container, corresponding to a predetermined mud-containing liquid quantity, and for also determining the Ponsar index of the mud using said apparent density and said decanted mud volume, whilst appropriately controlling the filling and emptying means.

According to a preferred embodiment of the measuring system according to the invention, the detection means comprise a detector system comprising at least one photoemitter and at least one photodetector, which are joined to one another and face one another on either side of said other container, whereby said other container and the clarified liquid are transparent to the light which can be emitted by each photoemitter, and means for displacing said detector system able to displace the latter along the other container, substantially from the bottom of the latter, and controlled by the electronic processing system, the photodetector then serving to inform said electronic processing system of the position of the separation surface between the decanted mud and the clarified liquid in the other container.

Preferably, the means for displacing the detector system comprise a stepping motor and the electronic processing system determines the number of steps during the displacement of the detector system substantially from the bottom of the other container.

The present invention finally also relates to a process for measuring the Ponsar index, used in the automatic measurement system also forming an object of the invention and wherein it comprises the following stages: filling the bottle with mud-containing liquid, filling the container with clarified liquid, filling the other container with a given clarified liquid quantity, filling the other container with a given mud-containing liquid quantity, immersing the bottle in the container, waiting for a given time to enable the bottle to reach a first stable position in the container, taking of measurements by the measuring system, calculation by the electronic processing system of a first quantity which is a function of the first position, raising the bottle, emptying and rinsing the same, filling the bottle with clarified liquid, immersing the bottle in the container, waiting for a given time until the bottle reaches a second stable position in the container, taking of measurements by the measuring system, calculation by the electronic processing system of a second quantity which is a function of the second position, calculation by the electronic processing system of the apparent density of the mud, with the aid of the first and second quantities, determination by said electronic system of the mud volume decanted or settled in the other container and determination by the electronic system of the Ponsar index on the basis of said volume and the apparent density of the mud.

In a preferred embodiment of the process according to the invention using the aforementioned boat, the stage of immersing the mud-containing liquid-filled bottle comprises the following stages: lowering the boat beneath the surface of the clarified liquid, waiting for a given time so as to permit the settling of the mud in the bottle and the impregnation of said bottle with clarified liquid, slight raising of the boat, which leads to the exhausting of the bottle beneath the surface of the clarified liquid and lowering the boat to the bottom of the container into a waiting position, whilst the immersion stage of the clarified liquid-filled bottle comprises the following stages:

lowering the boat beneath the surface of the clarified liquid, followed by a slight raising of said boat, which causes the exhausting of the bottle beneath the surface of the clarified liquid and lowering the boat to the waiting position.

BRIEF DESCRIPTION OF THE DRAWINGS

The invention is described in greater detail hereinafter relative to non-limitative embodiments and with reference to the attached drawings, wherein show.

DETAILED DESCRIPTION OF THE PREFERRED EMBODIMENTS

Figure 1:
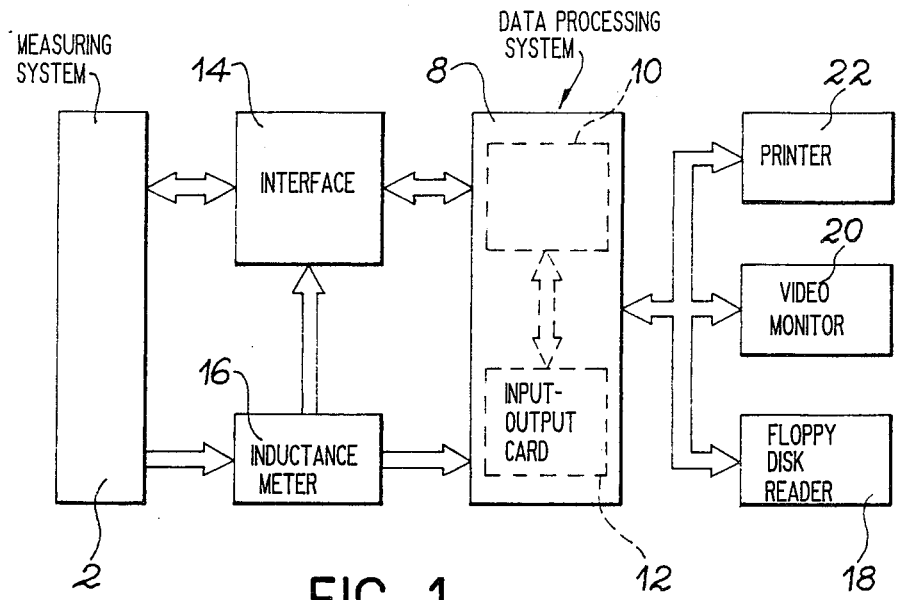
FIG. 1 Diagrammatically a special embodiment of the system for the automatic measurement of the Ponsar index according to the invention.
Figure 6:
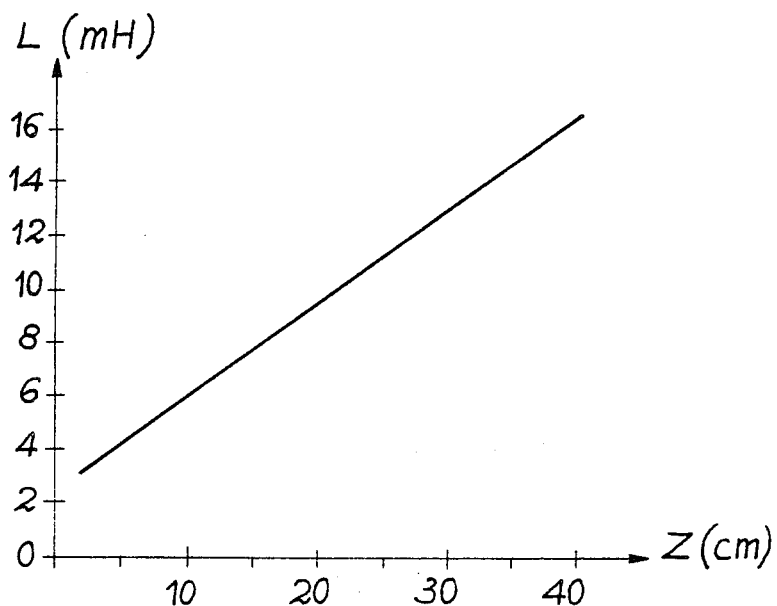
FIG. 6 A graph showing the inductance variations of a coil used in the apparent density measuring device, as a function of the lowering of the bottle into a container forming part of said device.

FIG. 1 diagrammatically shows a special embodiment of the system according to the invention for the automatic measurement of the Ponsar index. This index, which makes it possible to check the quality of the mud or sludge of purification or clarification stations and which, at all stages of the purification or clarification process, can be defined as the ratio V/P, in which V represents the volume settled in thirty minutes (generally expressed as milliliters), i.e. the deposit volume obtained after decanting or settling for thirty minutes of one liter of mud-containing liquid in 1½ liters of clarified liquid, and P represents the apparent density (or more precisely the apparent mass), expressed in grams, of one liter of mud-containing liquid, weighed in the same clarified liquid. The liquid is water in the case of a purification station and the latter will be used in exemplified manner hereinafter.

The system shown in FIG. 1 comprises:
- a system 2 comprising a device 4 for measuring the volume V (FIG. 2) and a device 6 for measuring the density P (FIG. 2), said system being positionable in a cabinet in which can also be located pumps, electrovalves and motors for the operation of these devices;
- a data processing system 8 having an e.g. GOUPIL 2-type computer 10, equipped with an input-output card 12 and which serves to control the devices and calculate the Ponsar index;
- a power interface 14 ensuring the connection between the data processing system 8 and the system 2 of the devices; and
- an induction meter 16 connected, in the manner shown in FIG. 1, to the system 2, to the data processing system 8 and to the interface 14 and which is used for measuring the apparent density P.

The data processing system 8 is also connected to a floppy disk reader 18, in which is stored the program permitting the operation of the automatic measurement system, as well as to a video monitor 20 permitting the display of the results of the measurements performed and to a printer 22 making it possible to retain the hard copy of these results.

Figure 2:
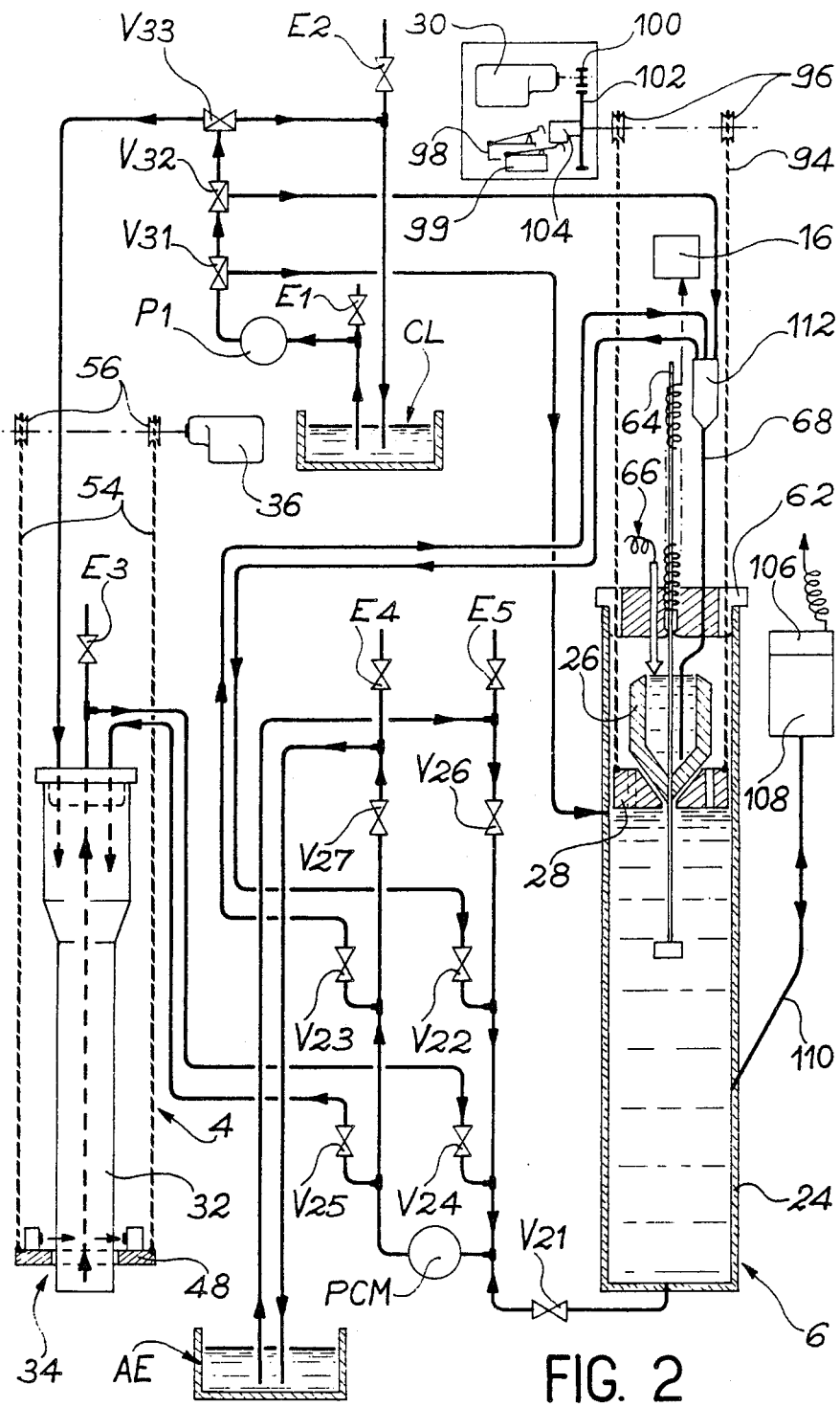
FIG. 2 A diagrammatic view of a device for measuring the decanted mud volume and a device for measuring the apparent density forming part of said system.

FIG. 2 diagrammatically shows the system 2 of devices 4 and 6. The apparent density measurement device 6 comprises an elongated, large capacity container 24, which can e.g. contain 20 liters and which is hereinafter called a "reservoir", as well as a bottle 26, a boat 28 making it possible to support said bottle and a motor 30 making it possible to move the boat 28 in reservoir 24.

The decanted mud volume measuring device 14 comprises another elongated container 32, which is hereinafter called a "cylinder", which has a capacity of e.g. 3 liters, together with a detector system 34 and a stepping motor 36 for moving the detector system 34 along said cylinder.

Cylinder 32 has a widened neck 36 (FIG. 3) which makes it possible to gently pour the mud-containing water onto the neck and consequently facilitate the settling of said mud in the clarified water with which the cylinder is to be filled. Moreover, the cylinder is closed e.g. by a Plexiglass cover 38, which has openings respectively permitting the passage of a tube 40 for filling the cylinder with clarified water, a tube 42 for filling said cylinder with mud-containing water and finally a tube 44 permitting the emptying thereof. The end of tube 44, which is located in the cylinder, is positioned in the vicinity of the bottom of said cylinder, whilst the ends of the tubes 40, 42, located in the said cylinder are slightly above the neck thereof. Cover 38 is also provided with an aeration opening 46.

The detector system 34 comprises a board 48, which is e.g. circular, which surrounds the cylinder 32 and can move along the latter. Board 48 carries at least one emitting photodiode 50 and preferably several such photodiodes, e.g. seven, oriented so as to transmit light beams through the cylinder 32, whereby the latter and the water are transparent to the light emitted by the photodiodes. Facing photodiodes 50, board 48 also carries a phototransistor 52 for receiving the light emitted by the photodiodes 50 and which has traversed cylinder 32, when it has not been prevented from doing so by the mud or sludge located in said cylinder.

The stepping motor 36 above cylinder 32 enables the board 48 to rise or fall along the cylinder, e.g. via cables 54, which connect the board to pulleys 56, whose rotation is controlled by stepping motor 36.

The measurement of the decanted mud volume is based on the following principle. After filling the cylinder with 1½ liters of clarified water and then 1 liter of mud-containing water, settling is allowed to take place for thirty minutes. At the end of this time, the board is moved from the bottom of the cylinder towards the top thereof by means of the stepping motor, whilst the photodiodes emit light beams. If the latter encounter the mud or sludge, which is opaque thereto, they are unable to reach the phototransistor. At the instant when the board reaches the separation level of the water and mud settled in the test piece, said light beams are able to pass through the cylinder and reach the phototransistor. The counting of the number of steps performed by the stepping motor 36 then makes it possible to determine the height of the decanted mud in the cylinder and obtain the volume of said decanted mud, because the cross-section of the cylinder is known.

On returning to the apparent density measuring device 6 (FIGS. 2 and 4), the latter comprises an electric measurement system, which is itself constituted by a coil 60 fixed to a support 62, which also serves as a cover for reservoir 24, as well as a metal rod 64 for forming the core of coil 60 and which is fixed to bottle 26, so that it can slit in the coil which is appropriately oriented for this purpose, when the bottle is moved in the reservoir.

The coil 60 is formed from several layers of metal wire turns, e.g. four copper wire layers, which are wound on to a glass tube. The coil is connected to the inductance meter 16, which makes it possible to measure the inductance. Support 62 of coil 60 has an opening permitting the passage of a probe 66 for detecting the filling of the bottle, together with a further opening permitting the passage of a tube 68 for filling and emptying said bottle. Holding and locking rings 70 are provided for maintaining in place the probe 66 and tube 68 with respect to the support 62.

Figure 4:
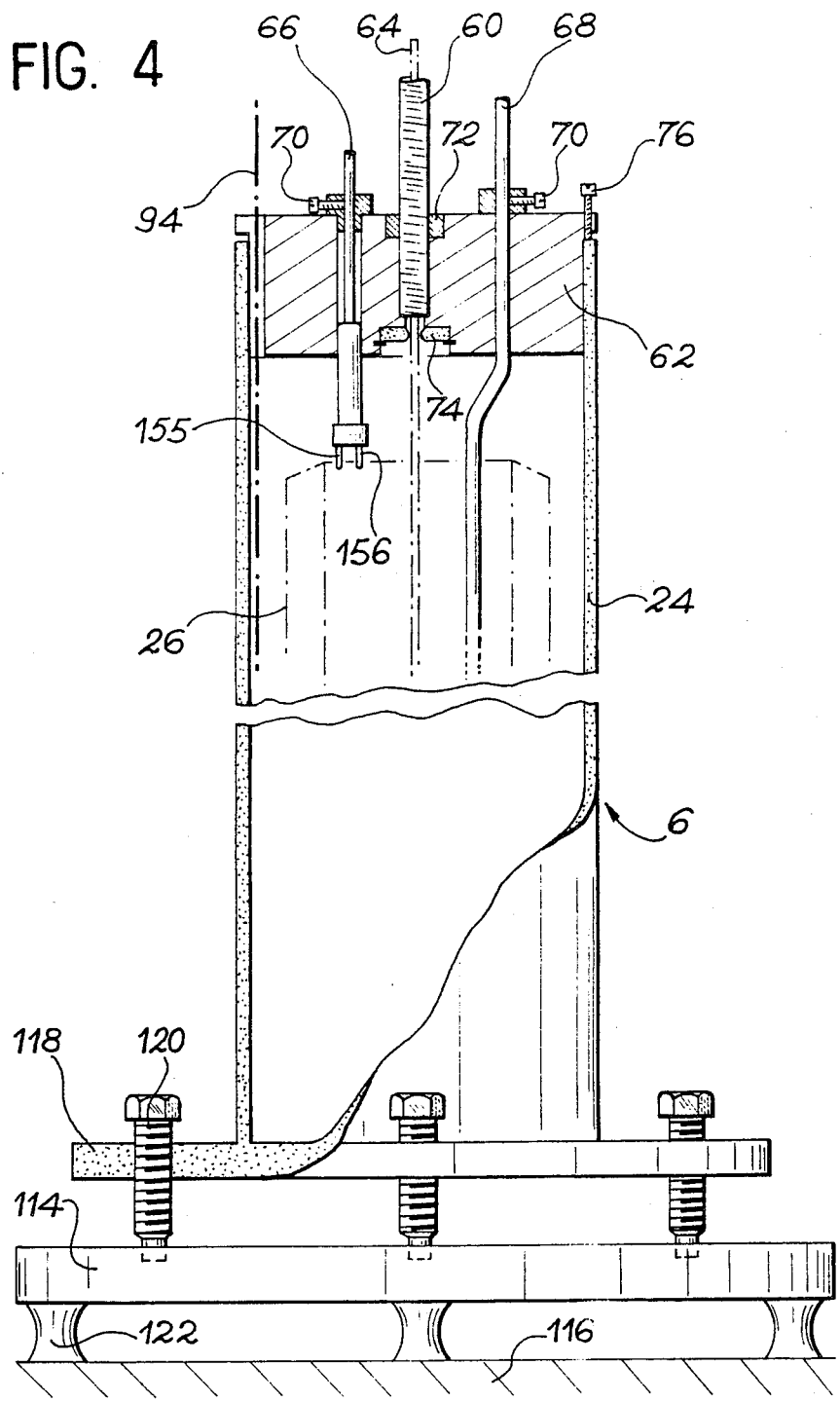
FIG. 4 A diagrammatic view of part of the device for measuring the apparent density.

Coil 60 extends above the reservoir 24 and parallel thereto. Mechanical coil regulating means 61 are provided for regulating said parallelism (FIG. 4). Another opening passing through support 62 receives the lower part of coil 60 fixed to support 62 via another holding and locking ring 72. Preferably, a polytetrafluoroethylene ring 74 is provided in the lower part of said other opening, so that it is traversed by the complete rod 64 before it enters the coil 60, when the bottle is displaced towards the top of the reservoir. Ring 74, which is held in place by an appropriate clip with respect to support 62, has an internal diameter less than the internal diameter of the glass tube and it makes it possible to reduce friction of the core in the glass tube of the coil, because otherwise such friction would lead to measuring errors. In addition, the presence of ring 74 prevents the formation of solid deposits along the glass tube, which could also lead to measuring errors. Screws 76 are also provided for regulating the orientation of support 62 with respect to the reservoir, so as to minimize said friction.

Rod 64, which forms the core of coil 60, is e.g. made from mild steel, which is surface treated by nickel-plating (KANIGEN process).

On its peripherary, support 62 is also provided with recesses permitting an air circulation between the interior and exterior of the reservoir, when the support is fitted thereon.

Bottle 26 (FIG. 5) is preferably made from polymethyl methacrylate (ALTUGLASS) and has an integrated float. Moreover, the shape of said bottle permits the "sliding" and discharge of air bubbles during the immersion of the bottle in the clarified water which the reservoir is intended to contain. More specifically, the bottle has a conical bottom 78, which is extended at the top by two coaxial cylindrical walls 80 and 82, which define between them an air-filled space 84, which serves as a float. This space is tightly sealed on one side by the bottom 78 of said bottle and on the other side by a ring-like part 86, fixed to the upper ends of walls 80 and 82. The assembly of the bottle parts is carried out by means of a commercially available glue suitable for the fixing of polymethyl methacrylate parts.

Boat 28 has a funnel-shaped opening 88 into which is to be fitted the bottom 78 of the bottle. Boat 28 also has holes 79 surrounding the funnel-shaped opening 88 and which serves to permit the flow of clarified water during the raising or lowering of the boat in the reservoir.

Rod 64 is fixed to the bottom 78 of the bottle and extends along the axis thereof. Rod 64 passes through the boat 28 via the opening 88 therein. Moreover, the lower end of rod 64 is provided with a ballast 92. The length of rod 64 is adequate to ensure that said ballast 92 does not strike against boat 28, when the latter is lowered to a waiting position indicated hereinafter.

Motor 30 is positioned above reservoir 24 and makes it possible to raise and lower the boat 28 with respect to reservoir 24 via cables 94 connecting boat 28 to pulleys 96, which are to be rotated by motor 30.

More specifically, motor 30 moves boat 28 between an upper position and a lower or waiting position in reservoir 24. In order to be able to accurately stop the boat in one or other of these positions, two level sensors 98, 99 with respect to the boat 28 and which are e.g. formed by two microcontacts are provided. In the embodiment of FIG. 2, a first spur or toothed ring 100, mounted on the spindle of motor 30, makes it possible to rotate a second spur or toothed ring 102 mounted on a common spindle for the two pulleys 96. The second ring has an appropriate step-down ratio compared with the first and which is a function of the level difference between the top and bottom positions of the boat 28, said ratio being e.g. equal to 5 in the embodiment of FIG. 2. A cam 104 is fixed to the second ring 102 and actuates one or other of the microcontacts 98, which is then raised to a logic level 0 or 1, as a function of its position.

The various bottle filling and emptying operations are performed when the boat is in the top position, the bottle, supported by the boat, then being in a raised position outside the clarified water of the reservoir.

Tube 68 is designed in such a way that its lower end is in the vicinity of the bottom of the bottle when the latter is in the raised position.

In order to control or check the filling of reservoir 24, a level sensor 106 is provided. It is e.g. a pressostat, which is triggered by an overpressure. This pressostat is fixed to an expansion vessel 108 connected by a pipe 110 to the low level of the reservoir. During the filling of the latter, the water rises in this pipe and leads to an overpressure in the expansion vessel, which triggers the pressostat when it is sufficiently high. The pressostat is brought to a logic level 0 when the reservoir is empty or during filling, and to a logic level 1 when the reservoir is full.

Figure 5:
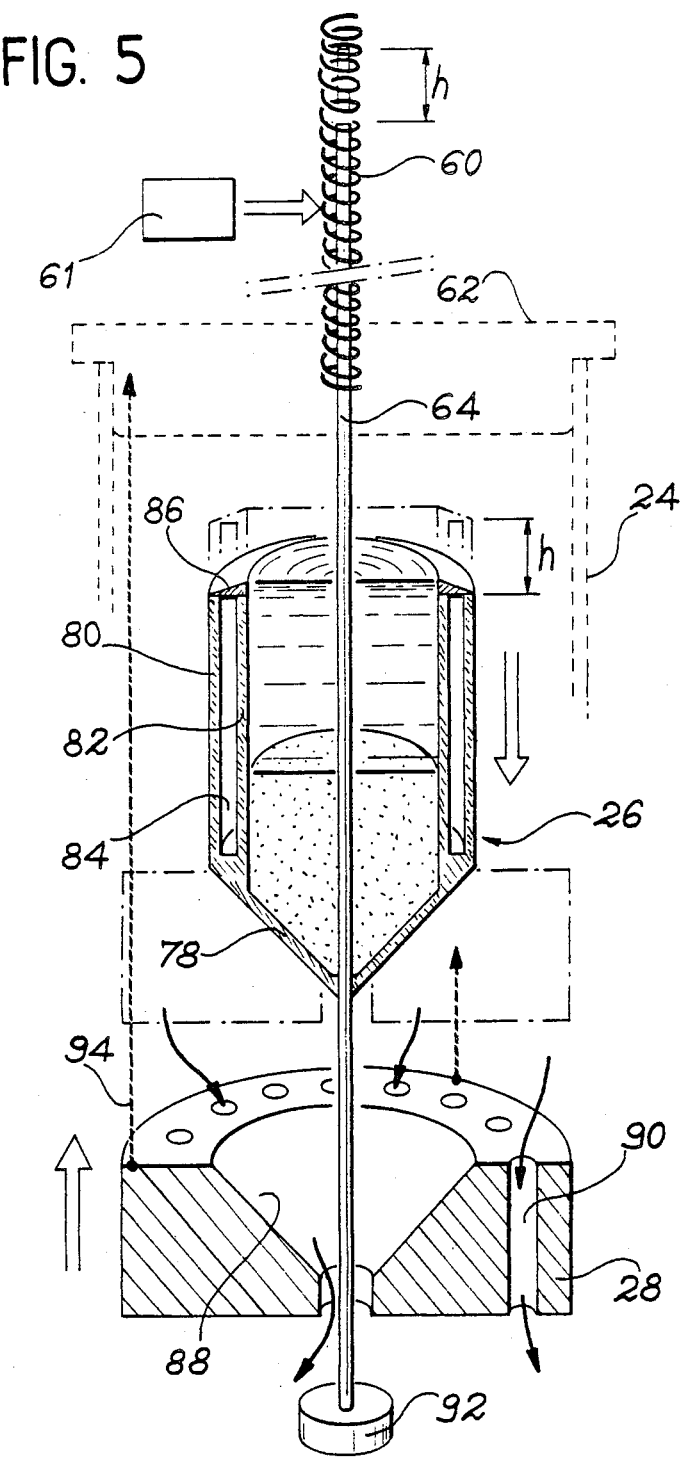
FIG. 5 A diagrammatic view of a special embodiment of the integrated float-equipped bottle using said apparent density measuring device.

The apparent density measurement principle is as follows. The apparent density is proportional to the immersion difference h, in the clarified water-filled reservoir, of the bottle 26 respectively filled with mud-containing water and clarified water (FIG. 5). The immersion difference h is proportional to the difference between the inductance L2 of the coil, corresponding to the equilibrium position of the bottle filled with mud-containing water in the reservoir, and the inductance L1 of the coil, corresponding to the position of the bottle filled with clarified water in said reservoir. Thus, the apparent density is proportional to said inductance difference. More specifically, the apparent density P is linked with the difference L2−L1 by the following formula:

$$P = (L2 - L1) R^{-1} \cdot S \cdot v^{-1} \cdot \mu \cdot g$$

in which R, S, v, $\mu$ and g respectively represent the slope of the line representing the variations of the coil inductance as a function of the lowering of the bottle, the cross-section of the coil core, the bottle volume, the density of the clarified water and the acceleration of gravity.

In the embodiment shown in FIG. 2, the slope R is 0.344 mH/cm, the core diameter 3 mm and the bottle volume 0.56 liters. The above formula then becomes:

$$P = 0.37 (L2 - L1)$$

in which the inductances are expressed in mH and the apparent density (for one liter of mud-containing water) in grams (i.e. when not taking account of the quantity g in the above formula).

Figure 14:
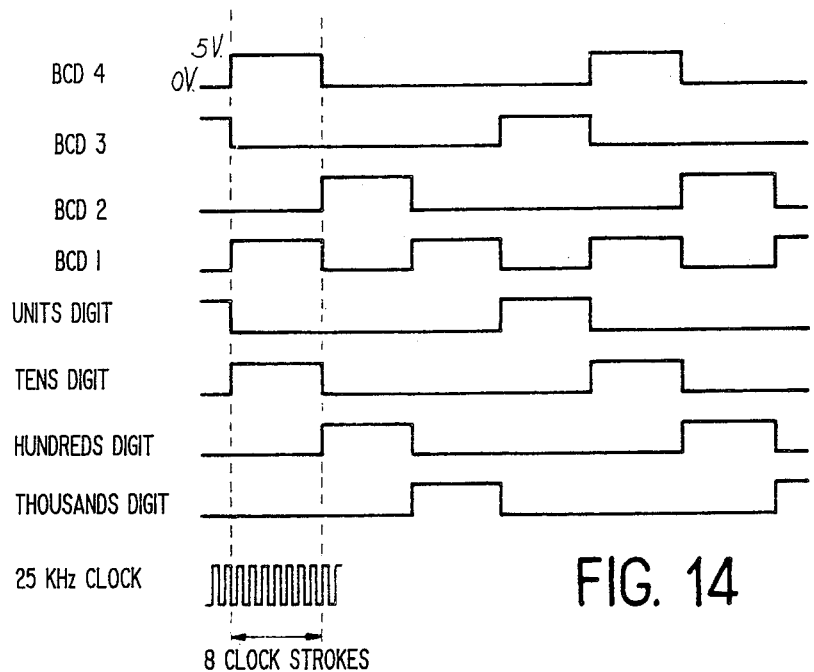
FIG. 14 A chronogram of signals supplied by this inductance meter.

The quantity R can be experimentally determined by plotting the variations of the inductance L of the coil, expressed in mH and measured with the aid of an inductance meter (cf. FIG. 14), as a function of the lowering or immersion Z of the bottle expressed in cm. As was shown hereinbefore, the quantity R is the slope of gradient of the thus obtained line.

When the bottle is in the raised position, rod 64 projects over the upper part of coil 60 but, during the respective measurements performed with the bottle filled with clarified water and with mud-containing water, the rod assumes an intermediate position between the top and bottom of the coil.

The weight of the ballast 92 is provided for this purpose, the length of the coil 60 and rod 64 being calculated in such a way that it is possible to weigh water containing a large amount of mud or sludge and also water containing a small amount thereof.

The interest of using polymethyl methacrylate for producing the bottle is based on the fact that said material is rapidly saturated with water and consequently the weight of the bottle is constant in the two phases of measuring the apparent density (bottle filled with mud-containing water and bottle filled with clarified water). The bottle can also be made from glass, which does not absorb water when immersed in it, the bottle weight also remaining constant in this case.

The measurement of the quantities P and V requires the filling of the cylinder with clarified water and sludge-containing water, as well as the emptying of said cylinder. It also requires the filling of the reservoir with clarified water and the emptying thereof. It also requires the filling of the bottle with clarified water and water containing sludge, together with the emptying of said bottle. These various filling and emptying operations are performed with the aid of two independent circuits of pumps and electrovalves, called "clarified water circuit" and "mud circuit". The clarified water source is constituted by the clarifier CL of the purification station and the mud-containing water source is constituted by the aerator AE of said station.

The clarified water circuit is as follows. The water is pumped into the clarifier by a pump P1, which is connected to one channel or way of a three-way or channel electrovalve V31, whereof a second way is connected to the reservoir 24, via a duct issuing into said reservoir, below the upper position of the boat, and whereof the third way is connected to one of the ways of a three-way electrovalve V32. A duct connects a second way of said electrovalve V32 to one of the channels of a four-channel distributor 112, which surmounts the coil support 62 and whereof a second channel is connected to tube 68. The third way of electrovalve V32 is connected to one way of an electrovalve V33, whereof a second way communicates with the clarifier via a duct, whilst its third way communicates with pipe 40 of the cylinder.

The pump P1 is e.g. a diaphragm pump ASTI 220V PC150. Electrovalves V31, V32 and V33 are e.g. BURKERT electrovalves of type 121, function F and with three ways. Thus, the following possible states exist for the clarified water circuit and for each state the opening or closing of the ways of the electrovalves is determined as a consequence:

wait: from CL to P1 to V31 to V32 to V33 to CL, filling the reservoir: from CL to P1 to V31 to the reservoir,
filling the bottle: from CL to P1 to V31 to V32 to the distributor,
filling the cylinder: from CL to P1 to V31 to V32 to V33 to the cylinder.

The emptying of the bottle, reservoir and cylinder take place via the mud circuit which will now be described. The mud or sludge-containing water is pumped into aerator AE by a pump PCM. A duct emanates from the aerator and leads to one way of a two-way electrovalve V26. The second way of said electrovalve is connected to one way of a two-way electrovalve V21. The second way of electrovalve V21 is connected to reservoir 24, into which it issues via its bottom.

On the duct connecting electrovalves V26 and V21 and as from electrovalve V26 are successively provided:
 a first branch leading to one way of a two-way electrovalve V22, whereof the second way leads to a third channel of distributor 112,
 a second branch leading to one way of a two-way electrovalve V24, whereof the second way is connected to pipe 44 (FIG. 3), and
 a third branch leading to the intake of pump PCM.

The outlet of pump PCM is connected to one way of a two-way electrovalve V27, whereof the second way is connected to the aerator. On the duct connecting pump PCM to electrovalve V27 and as from pump PCM are successively provided:
 a first branch leading to one way of a two-way electrovalve V25, whereof the second way is connected to pipe 42 (FIG. 5), and
 a second branch leading to one way of a two-way electrovalve V23, whose second way is connected to the fourth channel of the distributor 112.

The measurement of the settled volume in cylinder 32 requires a precise dosing of the mud-containing water quantity introduced into said cylinder, so that pump PCM is chosen on the one hand so as to be able to withstand the viscosity of the mud or sludge and on the other so as to ensure a constant flow rate. For example, it is possible to use a pump marketed under the reference PCM MOINEAU 03110. This pump PCM is controlled by a speed variator or controller making it possible to vary the flow rate.

Electrovalve V21 is e.g. a BURKERT function A electrovalve (normally closed). Electrovalves V22, V23, V24, V25, V26 and V27 are e.g., bearing in mind the viscosity of the mud or sludge, pneumatic JOUCOMATIC valves of series 212-213 with electric pilot valves which are normally open for electrovalves V26 and V27 or normally closed for electrovalves V22, V23, V24 and V25.

Thus, for the mud circuit, the following states exist and for each state, the opening or closing of the electrovalves is determined on the basis thereof:
 wait: from AE to V26 to PCM to V27 to AE,
 filling the bottle: AE to V26 to PCM to V23 to the distributor,
 filling the cylinder: AE to V26 to PCM to V25 to cylinder,
 emptying the cylinder: from cylinder to V24 to PCM to V27 to AE,
 emptying the bottle: from the distributor to V22 to PCM to V27 to AE,
 emptying the reservoir: from the reservoir to V21 to PCM to V27 to AE.

In order to prevent freezing, there is a system of vents by electrovalves E1, E2, E3, E4 and E5, which make it possible to "empty" the external circuits during the stoppage of the automatic measuring system according to the invention. Electrovalve E1 is branched on to the duct connecting pump P1 to the clarifier. Electrovalve E2 is branched on to the duct connecting electrovalve V33 to the clarifier. Electrovalve E3 is branched on the duct connecting electrovalve V24 to pipe 44. Electrovalve E4 is branched on to the duct connecting electrovalve V27 to the aerator. Finally, electrovalve E5 is branched on to the duct connecting the electrovalve V26 to said aerator.

Electrovalves E1 and E2 are e.g. BURKERT electrovalves, type 121, function B. Electrovalves E3, E4 and E5 are e.g. BURKERT vents, function B and normally open.

In order to reduce friction of core 64 in coil 60, it is appropriate for reservoir 24 and coil 60 to be as vertical as possible. For this purpose, the reservoir is placed on a support 114 (FIG. 4), which differs from the not shown support of cylinder 32. For this purpose, the bottom of the reservoir is mounted on a plate 118, whose horizontality can be regulated with the aid of three screws respectively passing through three holes at 120° from one another made in the plate 118 and threaded with the screw pitch, three notches being provided in the support 114 for receiving the respective ends of these screws. Furthermore, support 114 rests on the common frame 116 of devices 4 and 6, via rubber feet 122, in order to neutralize the vibrations produced by the pumps.

Figure 7:
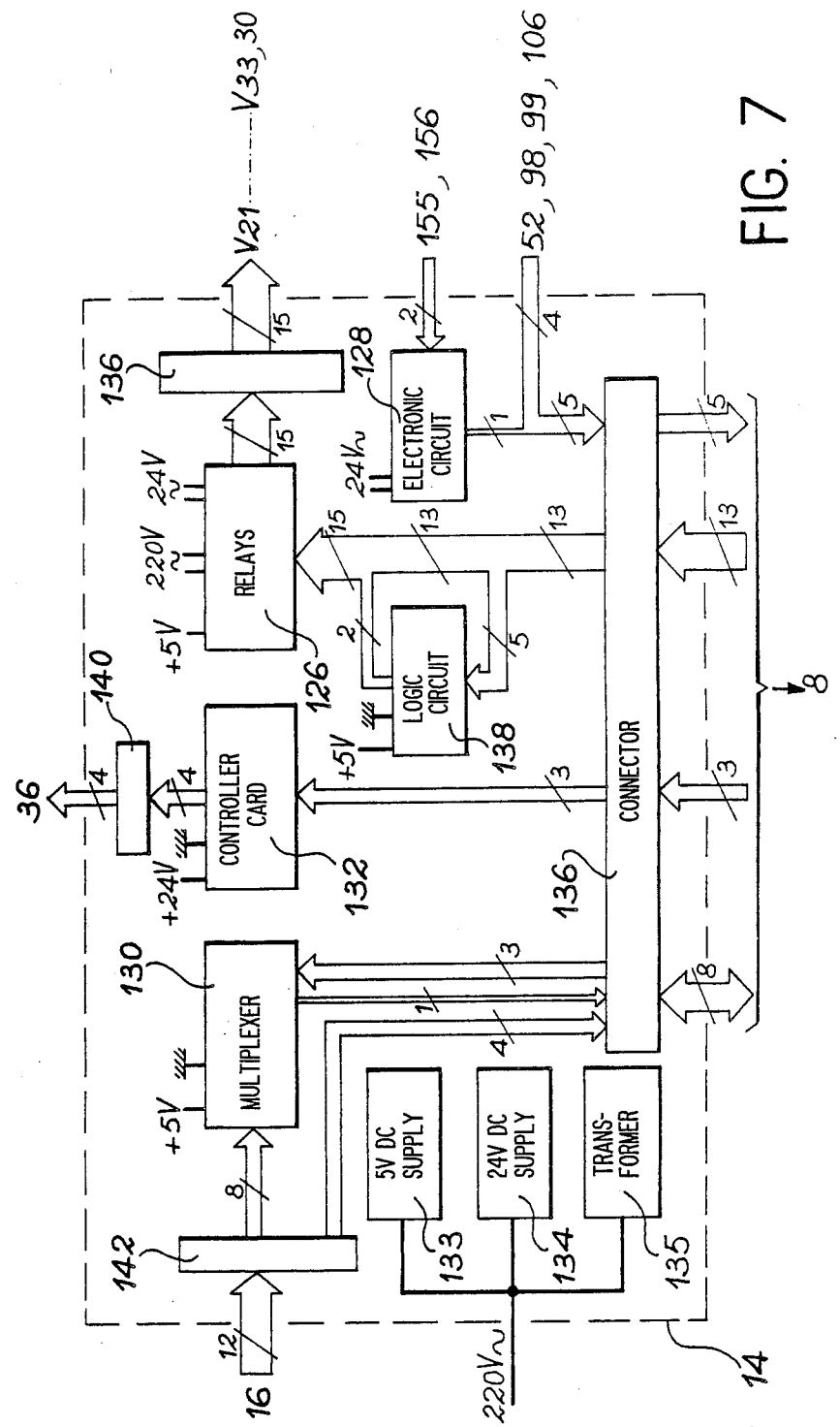
FIG. 7 A diagrammatic view of a power interface forming part of the automatic measuring system.

FIG. 7 diagrammatically shows the power interface forming part of the automatic measuring system according to the invention diagrammatically shown in FIG. 1. The function of this power interface is to convert the low or high voltage levels (in the considered example 0 V or 5 V) supplied by the GOUPIL computer into signals appropriate for bringing about operation of the electrovalves or motors; despatching and possibly rendering compatible with the data processing system, the informations from the various sensors 52, 98, 99 and 106 used in the measuring system according to the invention and to which reference has already been made; and to render usable by the computer, the signals from the inductance meter 16 (FIG. 13), which is connected to the terminals of coil 60 with a view to measuring the inductance thereof.

As can be seen in FIG. 7, the power interface comprises:
 a group 126 of relays for the control of the electrovalves and motor 30 of the boat,
 an electronic circuit 128 associated with probe 66,
 a multiplexer 130 receiving the signals from inductance meter 16,
 a card 132 for controlling the stepping motor 36, and
 supplies supplying the voltages and currents necessary for the operation of the electronics and electrical components of the cabinet, namely a stabilized +5 V d.c. supply 3A designated 133, a stabilized +24 V d.c. supply 1A designated 134 and an a.c. 120 VA 220 V-24 V transformer designated 135.

The output of the group 126 of relays is connected to the electrovalves and to motor 30 via plugs 136. The control signals of the relays from the data processing system 8 are transmitted to said relays via a 2×25 pin connector 136.

The power interface also comprises a logic circuit 138 corresponding to the relays controlling electrovalves V26 and V27. As can be seen in FIG. 7, circuit 138 is branched on to the transmission channel for the control signals for the relays from the data processing system 8.

Electrodes 155, 156 of probe 66 are connected to the input of electronic circuit 128. The signals from the sensors and circuit 128 are transmitted to the data processing system via connector 136. The control signals of card 132 are transmitted thereto by the data processing system, via connector 136 and the signals from said card 132 are transmitted to the stepping motor 36 via a plug 140.

As can be seen in FIG. 7, the output of inductance meter 16 is connected, via a connector 142, to one input of multiplexer 130 and to the data processing system 8 via connector 136, whilst by another input, multiplexer 130 receives signals from the data processing system 8 and transmits same thereto by an output, once again via connector 136.

FIG. 7 shows the number of lines of the different connecting channels connecting the various interface elements to one another and to various elements of the system (inductance meter, data processing system, etc.) in the special embodiment of the system described.

Obviously the two supply systems and the transformer referred to hereinbefore are supplied by the 220 V a.c. mains.

Figure 8:
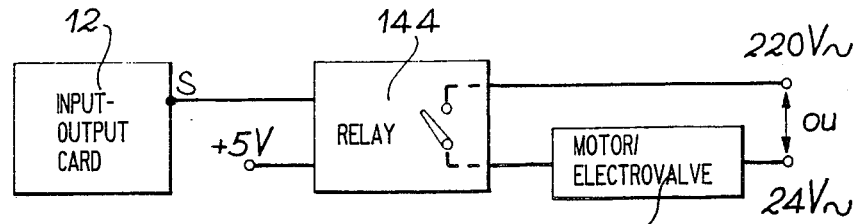
FIG. 8 A basic diagram of the control of electrovalves and a motor used in said system.

The control principle of the relays is as follows. The signals (0 or 5 V) from the input-output card 12 cannot directly control the electrovalves or motor 30 corresponding to the boat. Thus, said control is brought about via power relays able to switch high currents and high voltages. It is possible to use optoelectronic CELDUC relays, an example of which is designated 144 in FIG. 8. An input terminal of such a relay 144 is connected to an appropriate output S of the input-output card 12, whilst the other input terminal of relay 144 is brought to a constant voltage of +5 V. An output terminal of relay 144 is connected to an input terminal of the corresponding member 146 (motor 30 or electrovalve) and a voltage appropriate for the operation of said member (220 V a.c. or 24 V a.c.) is applied between the other output terminal of relay 144 and the output terminal of said member.

Thus, as motor 30 is controlled by two relays (see hereinafter), it has two input terminals, respectively associated with two output terminals and said relays. When output S is brought to a high voltage level (5 V), relay 144 is not energized and the motor is stopped (or the electrovalve is stable). When output S is at a low voltage level (0 V), the relay is energized and the motor operates (or the electrovalve is activated).

More specifically, the relays are used for controlling motor 30 making it possible to displace boat 28, said motor being supplied with 220 V a.c. and is controlled by two relays (one for the raising of the boat and the other for the lowering thereof) and electrovalves V21, V22, V23, V24, V25, V26, V27, V31, V32 and V33, which are supplied with 24 V a.c. Each of these electrovalves is controlled by a relay, with the exception of electrovalves V26 and V27, whose control will be explained hereinafter.

The other electrovalves E1, E2, E3, E4 and E5 are supplied with 24 V a.c. when the system according to the invention is rendered live.

Electrovalves V21, V22, V23, V24, V25, V26, V27, V31, V32 and V33 respectively have the following functions:
emptying the reservoir, emptying the bottle, filling the bottle with mud-containing water, emptying the cylinder,
filling the cylinder with mud-containing water, intake of mud-containing water, discharge of mud-containing water,
filling the reservoir with clarified water, filling the bottle with clarified water and filling the cylinder with clarified water.

The relays used are static CELDUC relays. These relays have a very considerable insulation between input and output (optoelectronic coupling), have an input circuit accepting a large control voltage variation (from 3 to 30 V) and permit an output on TRIAC with a current which can be up to 8 A.

The data processing system is equipped with two VIA 6522 circuits, as will be shown hereinafter and consequently has 32 inputs-outputs, whose direction (input or output) is determined during the programming of the system.

Figure 9:
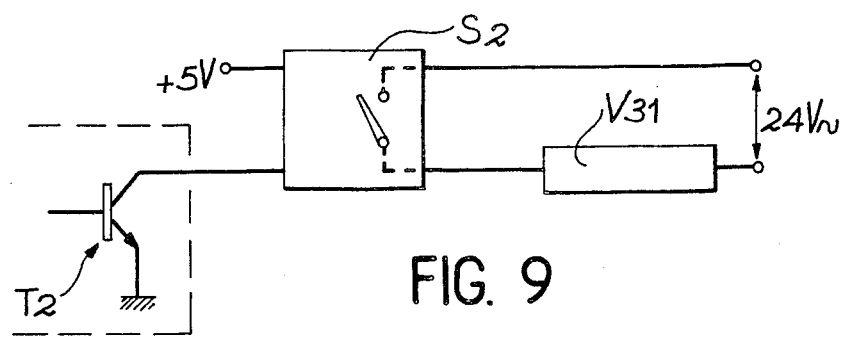
FIG. 9 An explanatory diagram of the control of said electrovalves.

Circuit VIA, which controls the relays is equipped with outputs having an open collector and all the ports are output-programmed. In the case of the control of electrovalves, the input stage of the relays serves as a load impedance. More specifically and as shown in FIG. 9, the control of each electrovalve, e.g. electrovalve V31 (obviously excepting electrovalves E1 to E5 and electrovalves V26 and V27, whose special case will be considered hereinafter) uses a transistor T2 for electrovalve V31 in the input-output card. It is e.g. a NPN transistor, whose emitter is grounded and whose collector is connected to an input terminal of the corresponding relay S2 for electrovalve V31, whilst the other input terminal of said relay is raised to a voltage of +5 V. An output terminal of said relay is connected to the input of electrovalve V31 and a 24 V a.c. voltage is established between the other output terminal of said relay and the output of electrovalve V31.

When the base of transistor T2 is brought to a logic level zero, said transistor is blocked, the relay is deenergized and electrovalve V31 does not operate. When the base of transistor T2 is brought to a logic level 1, said transistor is saturated, the relay is energized and the electrovalve operates. With regards to the motor 30 permitting the displacements of boat 28, for each of the relays associated with said motor, an appropriate, but not shown load impedance is mounted between the collector of the transistor and the input terminal of the corresponding relay. When the base of the transistor is brought to logic level zero, a voltage of 5 V is applied to the control card of the motor (negative logic).

With regards to the control of electrovalves V26 and V27, electrovalve V27 must be closed by the opening of electrovalve V25 or electrovalve V23 (inoperative, V25 and V23 are closed and V27 open).

Figure 10:
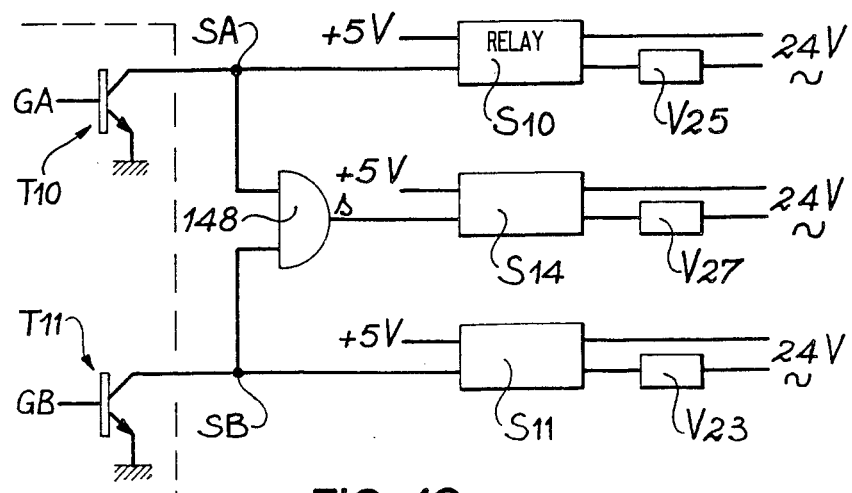
FIGS. 10 and 11 Diagrams explaining the control of other electrovalves of the automatic measurement system.

The presence of open collectors imposes a negative logic and the OR function (opening of V25 or V23) is brought about by means of a logic AND circuit according to the diagram of FIG. 10.

Electrovalve V25 is associated with relay S10 and transistor T10, whose base is GA, whilst electrovalve V23 is associated with relay S11 and transistor T11, whose base is GB, as explained for electrovalve V31 in the description of FIG. 9. Inputs SA and SB of an AND gate 148 are respectively connected to the collectors of transistors T10 and T11. The output s of AND gate 148 is connected to an input terminal of a relay S14 associated with electrovalve V27, whilst the other input terminal of said relay is raised to a voltage of +5 V. One output terminal of relay S14 is connected to the input of electrovalve V27 and a 24 V a.c. voltage is applied between the other output terminal of relay S14 and the output of electrovalve V27.

It is pointed out that SA is brought to logic level 0 (or 1) when GA is brought to logic level 1 (or 0) and SB is brought to logic level 0 (or 1) when GB is brought to logic level 1 (or 0). It is then possible to draw up the following table I, which gives the logic level of the output s as a function of the logic levels of GA and GB. This table shows that the desired function is obtained.

TABLE I

| GA | V25 | GB | V23 | s | V27 |
|---|---|---|---|---|---|
| 0 | closed | 0 | closed | 1 | open |
| 0 | closed | 1 | open | 0 | closed |
| 1 | open | 0 | closed | 0 | closed |
| 1 | open | 1 | open | 0 | closed |

Figure 11:
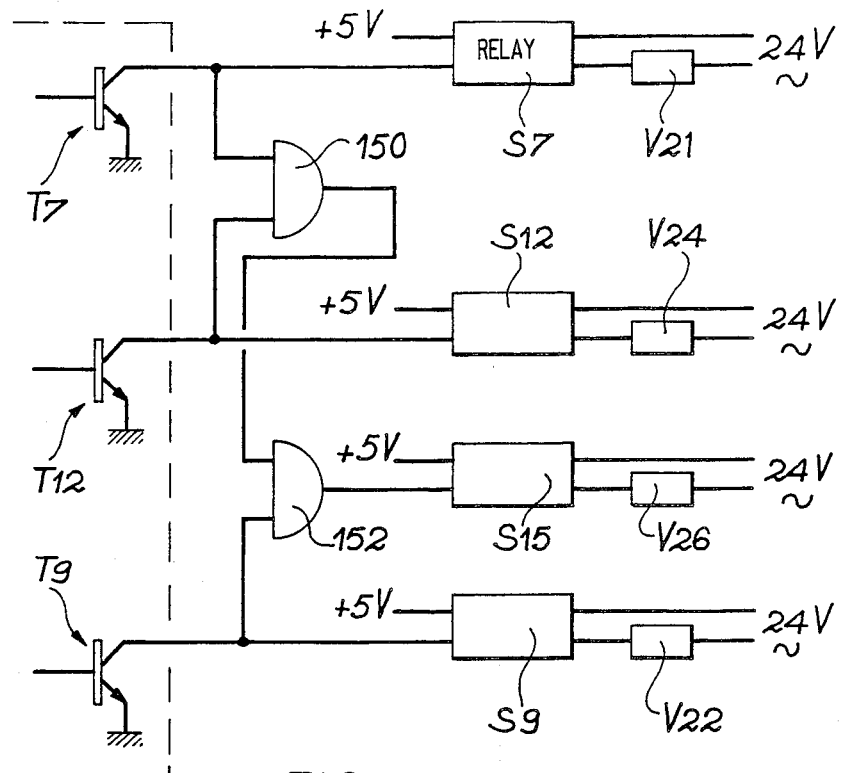

The control of electrovalve V26, which obeys the same principles, is brought about in the manner indicated in the diagram of FIG. 11 (cf. the information given hereinbefore regarding the states of the mud circuit). Electrovalve V21 (respectively V22 or V24) is associated with relay S7 (respectively S9 or S12) and transistor T7 (respectively T9 and T12), as was explained with respect to electrovalve V31 in the description of FIG. 9. In this case, use is made of two AND gates 150 and 152. The inputs of AND gate 150 are respectively connected to the collectors of transistors T7 and T12. One input of AND gate 152 is connected to the output of AND gate 150, whilst the other input of AND gate 152 is connected to the collector of transistor T9. The output of AND gate 152 is connected to one input terminal of the relay S15 corresponding to electrovalve V26, whilst the other input terminal of relay S15 is raised to a voltage of +5 V. One output terminal of relay S15 is connected to the input of electrovalve V26 and a 24 V a.c. voltage is applied between the other output terminal of relay S15 and the output of electrovalve V26.

For obtaining AND gates 148, 150 and 152, it is possible to use a circuit 74 LS 08 (quadruple AND), which is an integrated TTL circuit requiring a supply voltage of +5 V.

The signals from circuits VIA are available on connector 136 (FIG. 7) with 2×25 pins.

The sensors used in the invention make it possible to supply the data processing system with information on the state of the overall system. Certain of this information can be directly used (+5 V or 0 V signals), but other information has to be adapted by means of an appropriate electronic circuit. The sensors used are as follows:

pressostat 106, whose function is to detect the end of filling of the reservoir, which supplies a reading of 0 or 5 V and is directly connected to the data processing system (obviously via connector 136), the microcontact making it possible to detect the low position of the boat and which supplies a reading of 0 or 5 V, being also directly connected to the data processing system, the microcontact making it possible to detect the high position of the boat and which also supplies a reading of 0 or 5 V, also being directly connected to the data processing system, and phototransistor 52 making it possible to detect the mud-water separation in the measurement of the volume, which supplies a reading of 0 or 5 V and which is connected via a buffer circuit (AND gate) to the data processing system.

It is also possible to consider as a sensor, the electrodes of probe 66 indicating the end of bottle filling, which supply an electric resistance difference and are connected to the data processing system via circuit 128 (the resistance difference corresponding to a voltage level difference of 0 or 5 V).

No cylinder filling or emptying sensor is used, because the filling and emptying times thereof are programmed. There is also no sensor for detecting the board reaching its bottom position, because the board lowering time is also programmed. The operation of the pressostat (reservoir level sensor) and microcontacts (boat top and bottom level sensors) has already been explained in the description relative to FIG. 2.

Figure 12:
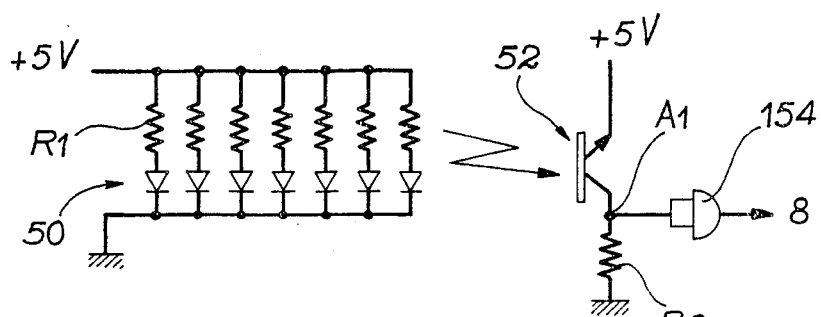
FIG. 12 An electronic diagram of a detection system used in the decanted mud volume measuring device.

The decanting or settling volume detection sensor is diagrammatically shown in FIG. 12. There are e.g. seven of the photodiodes 50 referred to in the description of FIG. 3 and they are of type TIL 32 (photodiodes emitting infrared radiation). For each of the photodiodes, the anode is connected to one end of a resistor R1, each of the other ends of resistors R1 being raised to a voltage of +5 V, whilst the cathodes of diodes 50 are all grounded. Each resistor R1 is e.g. 100 Ohms.

Figure 3:
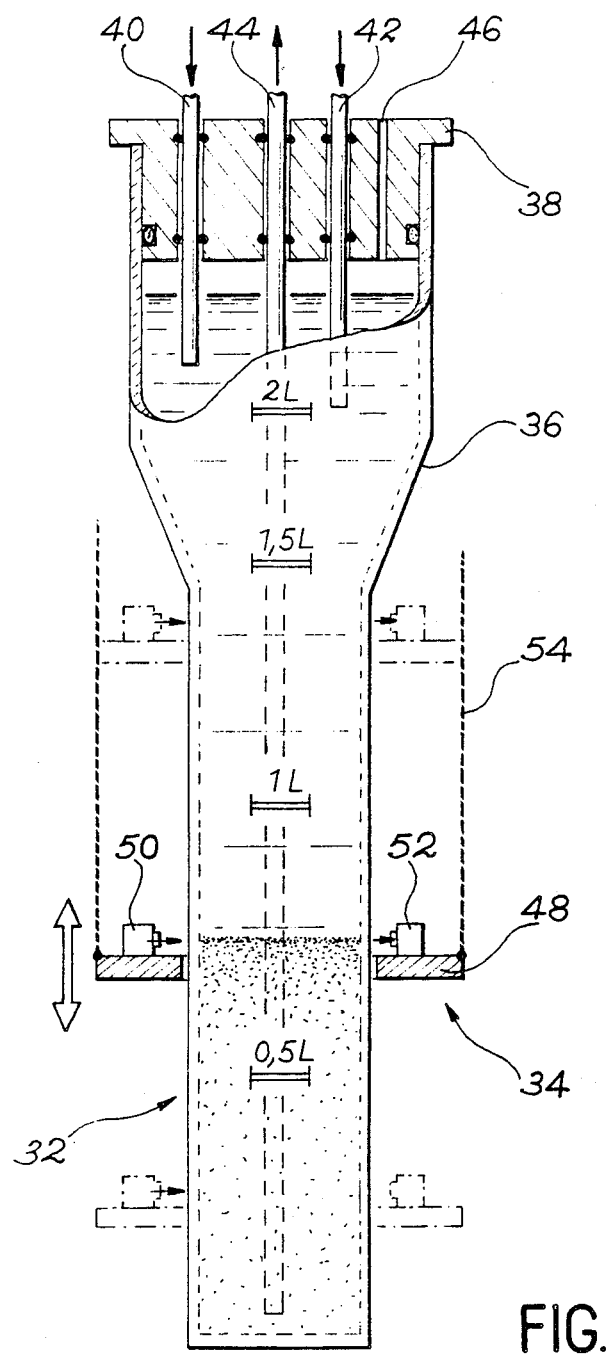
FIG. 3 A diagrammatic view of part of the device for measuring the decanted mud volume.

The phototransistor also referred to in the description of FIG. 3 is e.g. a phototransistor TIL 78. The emitter of said phototransistor is raised to a voltage of +5 V and its collector is connected to one end A1 of a resistor R2, whose other end is grounded. The sensor shown in FIG. 12 also comprises an AND gate 154, whose two inputs are connected to end A1 and the output to the data processing system 8. The AND gate is e.g. the remaining gate of circuit 74 LS 08 referred to hereinbefore. Resistor R2 is e.g. 3.6 kiloohms.

When the transistor is excited, point A1, bearing in mind the light emission of the diodes and bearing in mind the selected resistor R2, is raised to a voltage close to +5 V. When the transistor is no longer subject to the infrared radiation of the diodes, point A1 is brought to a voltage close to 0 V. The AND gate 154 acts as a buffer between phototransistor 52 and the input of the corresponding circuit VIA.

The bottle level detection probe makes it possible to detect the precise moment when the bottle is filled during its filling stage. The bottle must in fact be carefully filled, because if the electrovalves are closed too early, the bottle will only be partly filled and during the lowering of the boat, it will not be completely immersed because it is too light. Conversely, with respect to the filling with sludge-containing water, if the electrovalves close too late, there will be an overflow of sludge, which will enter the reservoir and lead to measuring errors.

In order to solve this filling problem, use is made of probe 66 provided with two electrodes 155, 156 (FIG. 4), which uses the principle of the resistance variation between two electrodes, which are e.g. of silver, when the latter are either in air, or immersed in a liquid, such as the clarified water or the mud-containing water. The probe position must be accurately regulated, because if it is positioned too low, the rising full bottle will immerse the electrodes and between these will form a water bridge, so that the "bottle full" information will be supplied to the data processing system, even when said bottle has been emptied and consequently the program will be stopped. If the probe is positioned too high, it will no longer detect anything.

Figure 13:
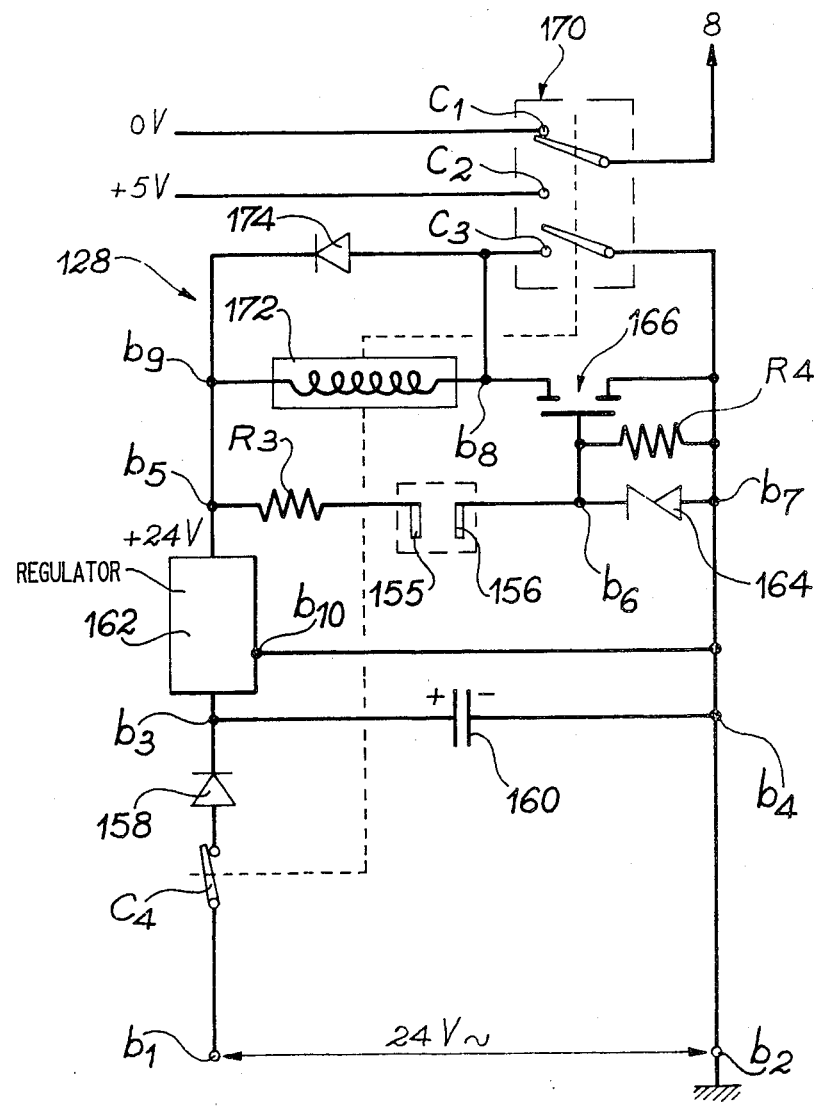
FIG. 13 A diagram of an electronic system associated with a probe for detecting the filling of the bottle.

The electronic circuit 128 (FIG. 7) associated with said probe 66 is diagrammatically shown in FIG. 13. This circuit is used for converting a difference between two electrical resistance values into a 0 V or +5 V level difference.

The circuit of the probe has two input terminals $b_1$ and $b_2$ between which is applied a 24 V a.c., terminal $b_2$ being grounded. This circuit firstly comprises means able to supply a stabilized 24 V d.c. voltage. These means comprise a rectifier diode 158, whose anode can be connected to terminal $b_1$ via a contact $c_4$ of a relay 170, to which reference will be made hereinafter. The cathode of diode 158 is connected to the input $b_3$ of a regulator 162. A filter capacitor 160 is connected by one end to input $b_3$ and by its other end to a point $b_4$, which is itself connected to $b_2$ and to another input $b_{10}$ of the regulator, provided for giving the 0 V level to the regulator.

A resistor $R_3$ is connected by one end to the output $b_5$ of regulator 162 and by its other end to electrode 155. A Zener diode 164 is connected by its cathode to a point $b_6$, which is itself connected to the other electrode 156, and by its anode to a point $b_7$, which is itself connected to point $b_4$. A resistor R4 is connected by one end to point $b_6$ and by its other end to point $b_7$.

The circuit shown in FIG. 13 also comprises a VMOS transistor 166, whose gate is connected to point $b_6$, whilst its source is connected to point $b_7$.

The circuit according to FIG. 13 also comprises a relay 170, whose output is connected to the data processing system via connector 136 and which has a first contact $c_1$ which, when it is activated, raises the relay output to voltage level 0 V, as well as a second contact $c_2$ which, when activated, raises said output to voltage level +5 V. Relay 170 also has an electromagnet 172, which is provided with a coil, whereof one end is connected to a point $b_8$, which is itself connected to the drain of transistor 166 and whereof the other end is connected to a point $b_9$, which is itself connected to point $b_5$.

Finally, a protective diode 174 is connected by its anode to a terminal of a third contact $c_3$ of the relay and by its cathode to point $b_9$. The anode of diode 174 is also connected to point $b_8$. In FIG. 13, the dotted lines indicate that the electromagnet 172 controls all the contacts $c_1$, $c_2$, $c_3$ and $c_4$.

In a purely illustrative and in no way limitative manner, diode 158 is a diode 1N 4004, capacitor 160 has a value of 900 μF, resistor R3 a value of 1.5 kiloohms, Zener diode is a diode DZ 10 V, resistor R4 has a value of 100 kiloohms, relay 170 is a 4RT 24 V relay and diode 174 is a 1N 4004 diode.

The 24 V a.c. voltage, following rectification and filtering gives, at the output of the regulator, a stabilized 24 V d.c. voltage. When the electrodes are in the air, no current can pass into resistor R3 and the VMOS transistor, whose gate is at potential 0 via resistor R4 does not conduct. The relay is deenergized and its output is brought to logic level 0, which is thus transmitted to the data processing system.

When the electrodes are immersed in a liquid, they have a low reciprocal electrical resistance permitting the passage of a current, which will then polarize the Zener diode. The gate of the VMOS transistor is then raised to a potential of 10 V making said transistor conductive, thus ensuring the activation of contact $c_2$ of the relay, which then supplies a logic level 1 to the data processing system.

The supplementary contact $c_3$, whereof the other terminal is connected to point $b_7$, ensures the self-holding of the relay, in order to prevent untimely vibrations and the other supplementary contact $c_4$ of relay 170 makes it possible to break said relay at the end of roughly 2 seconds after its excitation via capacitor 160, which discharges into the circuit. If at the end of theses 2 seconds, the electrodes are still immersed in the liquid, contact $c_2$ closes again and so on until the electrodes are out of the liquid. As soon as the liquid of the bottle reaches the electrodes, contact $c_4$ is open, capacitor 160 discharges for 2 seconds and ensures the self-holding of contacts $c_2$ and $c_3$ for this time.

Diode 174, which is connected in paralel on the terminal of the relay, is made conductive when said coil discharges and thus protects the VMOS transistor from the break induced current produced by the inductance of said coil.

Figure 15:
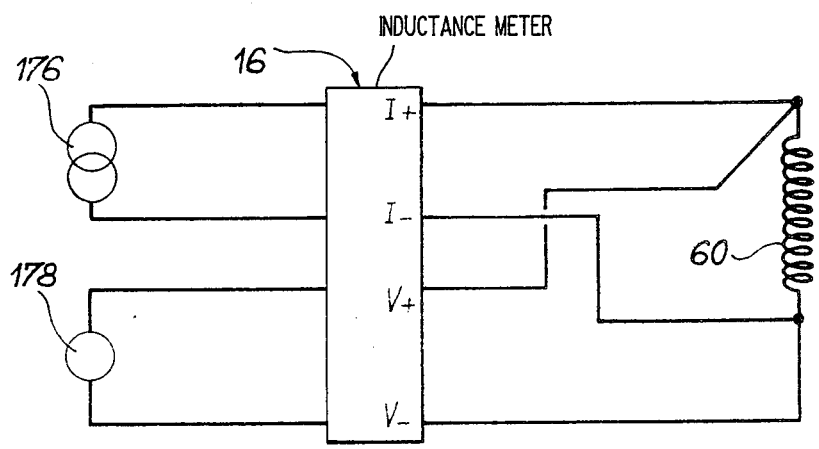
FIG. 15 A diagrammatic view of an inductance meter used in the apparent density measuring device.

FIG. 15 diagrammatically shows the inductance meter 16 making it possible to measure the inductance of coil 60. This inductance meter is e.g. of the type marketed by the Société Française D'Instrumentation under reference SAP 1 and which is provided with BCD (decimal binary coded) outputs, which are arranged in parallel. The so-called "4 wire" measuring principle has been adopted, which avoids any measurement falsified by the presence of parasitic inductances due to the connecting wires (case of so-called 2 wire measurement). The inductance meter, equipped with a constant current generator 176, applies to the terminals of coil 60 a constant amplitude sinusoidal current (10 μA) at a frequency of 1 KHz and at the same terminals measures the voltage obtained (max 2.7 V) by means of a voltmeter 178. This voltage, which varies with the value of the coil inductance so that, after calibration, the value of said inductance is obtained in millihenrys.

The coding of the measurement performed with the aid of the inductance meter will now be explained, said measurement taking place on 4 figures or digits (units, tens, hundreds, thousands). Each decimal digit (0 to 9) is coded on 4 bits BCD1, BCD2, BCD3 and BCD4, BCD1 representing the least significant bit and BCD4 the most significant bit.

The principle of parallel outputs is as follows. The selfmeter is provided with a 25 KHz clock. At the output of the inductance meter, there are 4 bits BCD1 to BCD4 and 4 bits indicating which digit is valid on BCD1 to BCD4 (digit of units, tens, hundreds, thousands). During eight clock strokes, one digit is supplied on BCD1 to BCD4 and then for the eight following clock strokes, the upper digit is supplied. When the thousands digit has been supplied, it is the units digit which is entered on BCD1 to BCD4. This is shown in the chronogram of FIG. 15, taking as an example the measurement of a value of $1294.10^{-2}$ mH.

In addition, the inductance meter has three binary outputs indicating the range over which the measurement is performed (microhenrys, millihenrys, henrys). Thus, there are eleven outputs, but their number has been reduced with the aid of the multiplexer 130 (FIG. 7). Preferably an analog multiplexer such as multiplexer 7503 AD, which requires a symmetrical supply of + and −15 V, is replaced by a TTL digital multiplexer of series 74 LS 151, which has 8 inputs and 1 output. This multiplexer has the advantage of only requiring a single voltage of +5 V (voltage which is in any case used and is therefore available in the system according to the invention) and a symmetrical supply of + and −5 V is unnecessary.

The stepping motor 36 (FIG. 2) is e.g. a motor marketed by the CROUZET company under reference 82 940 0, which is supplied by a constant voltage (24 V) electronic control card, which is also marketed by the CROUZET company under reference 84 854-6. From the data processing system, said card receives the control instructions: supply phases of the motor, rotation direction and control pulse.

Supply 133 is used for the TTL integrated circuits, the control stage of the relays and certain sensors, supply 134 for the control card of the stepping motor and tranformer 135 for supplying the circuit of the probe and the relays.

The input-output card used in the embodiment described with reference to the preceding drawings is card ESNOG 2020 marketed by the firm NOGEMA Informatique. This card controls 32 parallel input-outputs. It is equipped with two circuits VIA 6522, each of which occupies 16 addresses, i.e. 32 addresses for one card. The information relating to circuit VIA 6522 are given in GOUPIL documentation, vol. I or vol. IV.

Figure 16:
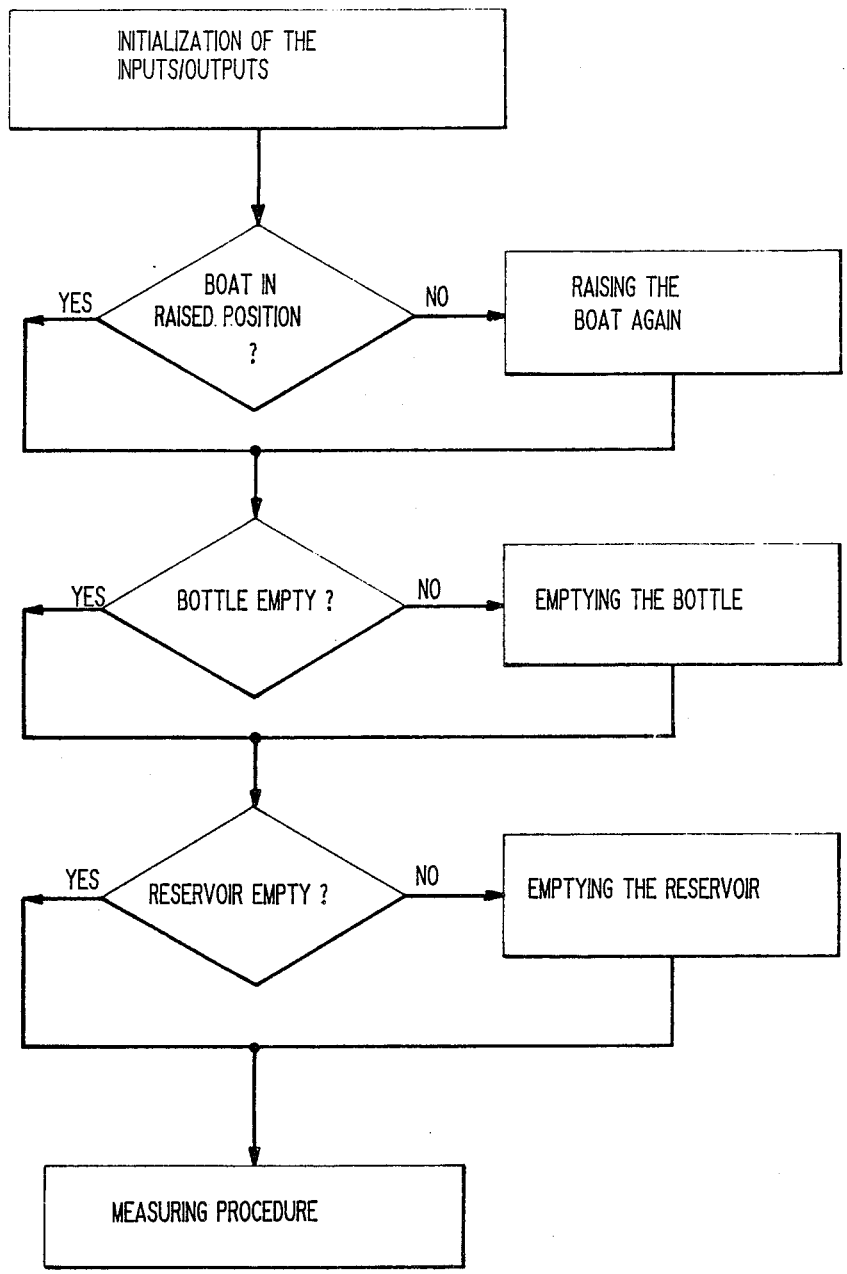
FIG. 16 A flow chart of an automatic measurement system control program.

FIG. 16 shows the general flow chart of the control program for the automatic PONSAR index measuring system according to the invention. Stage 1 of this program comprises initializing the input-outputs of the data processing system, followed by the checking of the state of system 2 constituted by the volume measuring device and the apparent density measuring device.

Thus, during the starting up of the computer, it is necessary to initialize the input-outputs thereof before supplying system 2. The effect of the initialization is to bring all the components of the system into the wait position (non-operating) by appropriately initializing each data register (through which pass the data both at the output and input) and each direction register (which configurates each port of the corresponding VIA circuit as input or output) associated with said data register for each of the VIA circuits.

The control of the state of system 2 is carried out by firstly checking whether the boat is in the raised position. If this is the case, a check is made to establish whether the bottle is empty. If the boat is not in the raised positioned, it is brought into said position and one then proceeds with checking the empty state of the bottle. If the bottle is empty, a check is then made to establish whether the reservoir is empty. If the bottle is not empty, it is emptied and one continues on to checking the empty state of the reservoir. If the reservoir is empty, the following successive stages incorporated into the control program and which will be indicated hereinafter are performed. If the reservoir is not empty, it is emptied and then the following stages 2 to 31 are performed and which will not be defined:

2—filling the bottle with mud-containing water.
3—Emptying the bottle (eliminating the mud which has been in the intake pipe.
4—Filling the bottle with mud-containing water.
5—Filling the reservoir with clarified water.
6—Filling the cylinder with clarified water (1.5 liters).
7—Filling the cylinder with mud-containing water (1 liter).
8—Lowering the boat a few centimeters beneath the surface of the clarified water of the reservoir (the bottle remaining level with the water).
9—Wait for 8 minutes (for the settling of the mud and the impregnation of the bottle with water).
10—Slight raising of the boat (leading to an exhaustion of the bottle beneath the water.
11—Lowering the boat into the lower position.
12—Wait for 10 minutes (for the stabilization of the bottle).
13—Perform coil inductance measurements (20 measurements).
14—Mathematical processing of these measurements and display of the result.
15—Raising the boat.
16—Emptying and rinsing the bottle.
17—Filling the bottle with clarified water.
18—Lowering the boat a few centimeters beneath the level of the clarified water of the reservoir and then slight raising the boat so as to immerse the bottle.
19—Lowering the boat into the lower position.
20—Wait for 4 minutes (for the stabilization of the bottle).
21—Perform the coil inductance measurements (20 measurements).
22—Mathematical processing of these measurements and display of the result.
23—Calculation of the apparent density of the mud and display the result.
24—Raise the boat.
25—Empty the bottle.
26—Reading the settling or decanting volume (board raised by stepping motor).
27—Putting back the board into place.
28—Display of the settling volume and the PONSAR index.
29—Empty and rinse the cylinder.
30—Empty the reservoir.
31—Stop the program.

It should be noted that when checking the state of the system 2, no check is made to establish whether the cylinder is empty, this being assumed because the programmed time for emptying the cylinder exceeds the time necessary for said emptying.

A subroutine makes it possible to time the waiting times (e.g. by calculating and expression such as sin (45°), whose calculation time is known).

Moreover, the control of the measuring process makes it necessary to check the sensors via input-output ports. The checking of the sensors is controlled by a single subroutine. The phases of the control program using this subroutine are phases 2, 4, 5, 11, 15, 17, 19, and 24. The subroutine in question checks the state of the sensor involved in the phase of the process. If this sensor is at logic level 0, the computer again checks the state of the sensor until it again passes to logic level 1. At this time an instruction is given to interrupt the phase. If at the end of a given number of tests, the state of the sensor is not equal to 1, the computer sill decide whether there is an abnormal operation of system 2 and is responsible for the fault. The process is interrupted and the subroutine in question then produces an error code corresponding to the sensor in question.

More specifically, the processing of the errors is carried out by means of two subroutines of the control program and consists, as a function of the particular case, either of checking that the configuration of the inputs-outputs is in accordance with that required before starting a new phase, or detecting the non-operation of a sensor, e.g. the probe, at the end of a sufficiently long predetermined time. It is also possible to provide a program for checking the sensors and control members one by one. For example, this program makes it possible, during a maintenance operation, to individually check these sensors and members in the case of a breakdown.

The control program used makes it possible to have a good coincidence between the automatic measurement performed and a manual measurement of the PONSAR index. Thus, the filling of the bottle with sludge-containing water is performed before that of the reservoir and cylinder in order to arrive at a decanting or settling rate of the sludge in the bottle of 30 minutes in accordance with what takes place during a manual measurement. The stabilization time of the bottle in the water of the reservoir during the measurement of the weight of the sludge has also been chosen for this purpose, the cylinder being filled with 1.5 liters of clarified water.

It should also be noted that the measurement of the weight of the sludge (bottle filled with sludge-containing water) is performed before measuring the tare (bottle filled with clarified water), which makes it possible to check the settling of the sludge and the impregnation of the bottle with water in a single operation.

Due to the fact that the bottle is filled with mud-containing water before the reservoir is filled with water gives 30 minutes between phases 2 and 13 (in accordance with the time recommended for manual measurement).

Moreover, the process used for obtaining the immersion of the mud-containing water-filled bottle uses the eddies produced by the movement of the boat to exhaust the bottle beneath the surface of the water (phase 10). Thus, the holes provided in the boat enable the water to flow out during the boat raising or lowering movements. When the boat rises, there is a water flow from top to bottom, which can make it possible to lower the bottle. More specifically, following the end of the filling of the cylinder with sludge-containing water, the boat is lowered and immobilized beneath the surface of the water. The thus freed bottle remains on the surface and floats level with the water. Once the settling time has been reached, the boat is raised by a few centimeters, which induces a downward current exhausting the bottle beneath the surface of the water. The boat is then immobilized for a few moments (e.g. a few seconds) to enable the bottle to start its descent without disturbance. The boat is then brought into the lower position.

This hydraulic exhaustion solution adopted for immersing the bottle has the advantage, e.g. compared with a mechanical system, of being very easy to perform by programming.

It is finally pointed out that the times separating phases 2 (filling the bottle with sludge-containing water) and 13 (inductance measurements) and phases 7 (filling the cylinder with sludge-containing water) and 26 (reading the settling volume) are both equal to 30 minutes.

In the case of a failure in the data processing system, it is possible to provide manual control means for system 2. To this end, it is possible to use a transparent reservoir having marks, so that it is possible to accurately fill it and correctly position the boat, together with a graduated cylinder permitting the direct reading off of the settling volume. During a manual measurement, the data processing system and power interface are disconnected.

Moreover, with respect to the measurement of the mud volume settled in the cylinder, following the number of steps performed by the stepping motor controlled by the computer in order to obtain the settling limit have been recorded, the settled mud volume is calculated by the following formula:

$$V1 = F \times V2 + V0$$

in which V1 represents the settled mud volume, F the number of steps and V2 the volume corresponding to each step. The quantity V0 is an initial volume due to the fact that the board does not precisely start from a zero height. Quantities V0 and V2 can be determined during the calibration of the apparatus. In the considered embodiment, the quantites V0 and V2 are respectively equal to 96.774 ml and 4.516 ml.

Finally, with regards to the taking of measurements by the inductance meter, the values measured by it are stored in the computer and then processed. However, certain measurements can be aberrant due to the build-up time of the output signals of the multiplexer. To obviate this disadvantage, it is merely necessary to carry out an appropriate statistical processing of the measurements made by the inductance meter. The number of measurements (20) indicated in phases 20 and 21 is only given as an example and said number could obviously be higher or lower than 20.

This processing is preferred in the following way by the computer. After acquiring and storing 20 inductance values (corresponding either to quantity L1 or to quantity L2 referred to hereinbefore), values which can be designated M1, M2 ..., M20, the mean value M and the standard deviation $\alpha$ of these values are calculated. s5 is the first value between M$-\alpha$ and M$+\alpha$. Any value not belonging to the range M$-\alpha$ M$+\alpha$ is replaced by s5. At the end of this, each number M1 to M20 is between M$-\alpha$ and M$+\alpha$. Thus, all the aberrant values are eliminated and it is possible to calculate a new mean value, which will be looked upon as the inductance value. Thus, knowing the two values L1 and L2 of said inductance, the program calculates the apparent density P on the basis of the formula given hereinbefore, or more specifically on the basis of the formula:

$$P = 0.41(L2 - L)$$

in which the coefficient 0.41 was determined during the calibration of the apparatus.

As system 2 is enclosed in a cabinet or more generally in an enclosure which is opaque to sunlight, there is no over-activation of the mud or sludge during the measurement and light does not reach the phototransistor 52, which would falsify the measurements.

What is claimed is:

1. An apparatus for measuring the apparent density of a mud contained in a liquid, comprising:
   a container,
   means for filling the container with clarified liquid and for emptying the same,
   a bottle able to float in the container when said container is filled with clarified liquid and when the bottle is empty,
   means for displacement of the bottle for bringing said bottle into the clarified liquid of the container and removing the same, means for filling said bottle with clarified liquid, for filling said bottle with liquid containing mud and for emptying said bottle, said bottle being provided with enabling means for enabling the bottle to reach, in the container filled with clarified liquid, two equilibrium positions which respectively correspond to the bottle filled with clarified liquid and to the bottle filled with liquid containing mud, an electrical measuring system able to supply an electric signal, which is a function of the position of said bottle in said container, and an electronic processing system for determining the apparent density of one volume of the liquid containing mud, weighed into the clarified liquid, on the basis of electric signals corresponding to the positions in the clarified liquid-filled container, of the bottle respectively filled with clarified liquid and mud-containing liquid, by appropriately controlling the filling and emptying means and the displacement means of said bottle.

2. An apparatus according to claim 1, wherein the bottle has an integrated float and an external shape making it possible to discharge air bubbles during the immersion of the bottle in the clarified liquid.

3. An apparatus according to claim 2, wherein the bottle has a conical bottom and comprises a cylindrical outer wall and an inner wall, which define between them a space which is tightly sealed.

4. An apparatus according to claim 1, wherein the bottle is made from a material which, when immersed in the clarified liquid, does not absorb the latter.

5. An apparatus according to claim 1, wherein said means enabling the bottle to reach the two equilibrium positions comprise a rod which is fixed to the bottle and projects over the surface of the clarified liquid of the said container, when the bottle is filled with clarified liquid and when the bottle is filled with liquid containing mud.

6. An apparatus according to claim 1, wherein it also comprises an electrode-incorporating probe for informing the electronic processing system of the filling of the bottle.

7. A system for measuring the Ponsar index of a mud or sludge contained in a liquid, wherein it comprises the apparent density measuring system according to claim 1, another container, means for filling with clarified liquid, filling with mud-containing liquid and emptying said other container, electric detection means able to supply other electric signals, which are a function of the mud level decanted or settled in said other container previously filled with clarified liquid and mud-containing liquid and wherein the electronic processing system also serves to determine, on the basis of said other signals, the mud volume decanted or settled in said other container, corresponding to a predetermined mud-containing liquid quantitty, and also to determine the Ponsar index of the mud using said apparent density and said decanted mud volume, whilst appropriately controlling the filling and emptying means.

8. A system according to claim 7, wherein said detection means comprise a detector system comprising at least one photoemitter and at least one photodector, which are joined to one another and face one another on either side of said other container, whereby said other container and the clarified liquid are transparent to the light which can be emitted by each photoemitter, and means for displacing said detector system able to displace the latter along said other container, substantially from the bottom of the latter and controlled by the electronic processing system, the photodetector then serving to inform said electronic processing system of the position of the separation surface between the decanted mud and the clarified liquid in said other container.

9. A system according to claim 8, wherein the means for displacing the detector system comprise a stepping motor and wherein the electronic processing system serves to determine the number of steps during the displacement of the detector means substantially from the bottom of said other container.

10. An apparatus according to claim 1, wherein the means for filling the bottle with clarified liquid, for filling the bottle with liquid containing mud and for emptying the bottle comprise:
 a tube which is fixed with respect to the said container and which has a lower end in the said container, said lower and being in the vicinity of the bottom of the bottle when the said bottle is removed from the clarified liquid of the said container,
 a clarified liquid circuit for the circulation of said clarified liquid, said clarified liquid circuit being able to send said clarified liquid into the other end of said tube by the intermediate of valves which are controlled by the electronic processing system, and
 a mud circuit for the circulation of said liquid containing mud, said mud circuit being able to send said liquid containing mud into the other end of said tube and to pump said clarified liquid from said other end, by the intermediate of other valves which are also controlled by the electronic processing system.

11. An apparatus according to claim 1, wherein the bottle is made from a material which, when immersed in the clarified liquid, is rapidly saturated with said clarified liquid.

12. An apparatus according to claim 1, wherein the bottle displacement means comprise a boat able to support the bottle and electric means for displacing the boat, said electric means for displacing the boat being controlled by said electronic processing system.

13. An apparatus according to claim 12, wherein said boat has holes permitting the circulation of the clarified liquid.

14. An apparatus according to claim 5, wherein the electrical measuring system comprises a coil, which is fixed with respect to the container, said rod being a metal rod rendered integral with the bottle and able to form a core for the coil and slide therein when the bottle is displaced in the container, thus modifying the inductance of the coil, and means for measuring a magnitude which is a function of said inductance, said means being able to supply said electric signal.

15. An apparatus according to claim 14, wherein the measuring means comprise an inductance meter.

16. A process for measuring the Ponsar index of a mud or sludge contained in a liquid, comprising the steps of:
 filling a bottle with mud-containing liquid,
 filling a first container with clarified liquid,
 filling a second container with a given clarified liquid quantity,
 filling said second container with a given mud-containing liquid quantity,
 immersing said bottle in said first container, waiting for a given time to enable said bottle to reach a first stable position inn said first container, taking of measurements by a measuring system which supplies an electric signal as a function of the position of said bottle in said first container, calculation by an electronic processing system which determines the apparent density of one volume of the liquid containing mud, weighed into the clarified liquid, on the basis of said electric signals corresponding to the positions in the clarified liquid-fill container, of the bottle respectively filled with clarified liquid and mud-containing liquid, by appropriately controlling the filling and emptying and the displacement of the bottle, wherein said calculation produces a first quantity which is a function of a first position, raising the bottle, emptying and rinsing said bottle, filling the bottle with clarified liquid, immersing the bottle in said first container, waiting for a given time until the bottle reaches a second stable position in said first container, taking of measurements by said measuring system, calculation by said electronic processing system of a second quantity which is a function of said second position, calculation by said electronic processing system of the apparent density of the mud based upon the first and second quantities, determination by said electronic system of the mud volume decanted or settled in said second container and determination by the electronic system of the Ponsar index on the basis of said volume and the apparent density of the mud.

17. The process according to claim 16, wherein said bottle is made from a material which, when immersed in a clarified liquid, is rapidly saturated with said clarified liquid and wherein the step of immersing the bottle filled with mud-containing liquid comprises the following steps:

utilizing a boat which supports said bottles and has holes permitting the circulation of said clarified liquid, lowering said boat beneath the surface of the clarified liquid, waiting for a given time so as to permit the settling of the mud in the bottle and the impregnation of said bottle with clarified liquid, slightly raising said boat, which leads to the exhausting of the bottle beneath surface of the clarified liquid and lowering the boat to the bottom of said first container into a waiting position, wherein the immersion step of the clarified liquid-filled bottle comprising the following steps: lowering said boat beneath the surface of the clarified liquid, followed by a slight raising of said boat, which causes the exhausting of the bottle beneath the surfsce of the clarified liquid and lowering the boat to the waiting position.

* * * * *